(12) United States Patent
Diemer

(10) Patent No.: US 8,644,942 B1
(45) Date of Patent: Feb. 4, 2014

(54) METHOD AND APPARATUS FOR TREATING TISSUE

(75) Inventor: Joel A. Diemer, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 1564 days.

(21) Appl. No.: 11/670,878

(22) Filed: Feb. 2, 2007

Related U.S. Application Data

(60) Provisional application No. 60/764,915, filed on Feb. 2, 2006.

(51) Int. Cl.
*A61N 1/05* (2006.01)

(52) U.S. Cl.
USPC .......................................................... 607/51

(58) Field of Classification Search
USPC ...................................... 607/50, 51
See application file for complete search history.

(56) References Cited

U.S. PATENT DOCUMENTS

| | | | |
|---|---|---|---|
| 4,026,304 A | 5/1977 | Levy | |
| 4,313,438 A | 2/1982 | Greatbatch | |
| 4,314,554 A | 2/1982 | Greatbatch | |
| 4,549,547 A | 10/1985 | Brighton et al. | |
| 4,556,051 A | 12/1985 | Maurer | |
| 4,846,181 A | 7/1989 | Miller | |
| 4,982,742 A | 1/1991 | Claude | |
| 4,989,605 A | 2/1991 | Rossen | |
| 5,395,398 A | 3/1995 | Rogozinski | |
| 5,397,338 A | 3/1995 | Grey et al. | |
| 5,433,735 A * | 7/1995 | Zanakis et al. | 607/50 |
| 5,935,156 A | 8/1999 | Chandler et al. | |
| 6,535,767 B1 | 3/2003 | Kronberg | |
| 6,607,500 B2 | 8/2003 | Da Silva et al. | |
| 6,937,905 B2 | 8/2005 | Carroll et al. | |
| 6,988,005 B2 | 1/2006 | McGraw et al. | |
| 2004/0015189 A1 | 1/2004 | McGraw et al. | |
| 2004/0054379 A1 | 3/2004 | Carroll et al. | |
| 2004/0176828 A1* | 9/2004 | O'Brien | 607/119 |
| 2006/0030906 A1 | 2/2006 | Carroll | |
| 2006/0136048 A1* | 6/2006 | Pacetti et al. | 623/1.42 |

\* cited by examiner

*Primary Examiner* — Eric D. Bertram

(74) *Attorney, Agent, or Firm* — Deborah A. Peacock; Jeffrey D. Myers; Peacock Myers, P.C.

(57) ABSTRACT

A method and apparatus for treating tissue of a patient with an implantable material comprising a plurality of electrodes for providing controlled microcurrent stimulation.

49 Claims, 3 Drawing Sheets

METHOD AND APPARATUS FOR TREATING TISSUE

CROSS-REFERENCE TO RELATED APPLICATIONS

This application claims priority to and the benefit of the filing of U.S. Provisional Patent Application Ser. No. 60/764,915, entitled "Microcurrent Assisted Bone/Tissue Repair System (OSEFX)," filed on Feb. 2, 2006, and the specification thereof is incorporated herein by reference.

BACKGROUND OF THE INVENTION

1. Field of the Invention (Technical Field)

The present invention relates to a medical apparatus and process to treat and assist bone and tissue repair and regeneration.

2. Description of Related Art

Stress-induced microcurrents in the development and maintenance of bone strength and healing in both tissue and bone, following fractures or other trauma, can aid conventional modalities in the treatment of persistent infections, burns, and a variety of other conditions including bone repair.

The application of electrical energy to injured tissues has been an acceptable mode of medical therapy for many years and is well characterized. Application of electrical stimulation can promote wound healing and low intensity direct current stimulation can be switched between negative and positive polarities during the course of treatment. Traditional microcurrent electrotherapy treatment produces a series of microcurrent waveform signals that are directed to a selected treatment area of a human or animal. Historically electrotherapy methods primarily utilized only a single waveform and/or current setting for the duration of the treatment but more recently multiple forms have become common.

The following are examples of such implanted systems that deliver electrical pulses to repair tissue. Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

U.S. Pat. No. 4,982,742 to Claude, entitled "Apparatus and Method to Facilitate Healing of Soft Tissue Wounds", issued Jan. 8, 1991, discloses a method for applying therapeutic microcurrent excursions and a bandage containing circuitry for generating microcurrent excursions comprising an assemblage with two electrodes and a power supply. U.S. Pat. No. 4,556,051 to Maurer, entitled "Method and Apparatus for Healing Tissue," issued Dec. 3, 1985, discloses a method for promoting healing with interacting electric current and a magnetic flux field and electrodes adhesively attached to skin adjacent the injured tissue, and discloses a variation of an externally applied two electrode electrostimulator device in combination with an apparatus to simultaneously produce magnetic field pulses. U.S. Pat. No. 6,607,500 to Da Silva et al., entitled "Integrated Cast and Muscle Stimulation System," issued Aug. 19, 2003, disclose a device that allows electrical stimulation, in the form of a variety of electrical pulse formats to an anatomical site under a cast. The device described is a variation of the externally applied two electrode electrostimulator device to enhance tissue healing or bone growth and alternatively a cast embedded TENS device to mitigate muscle atrophy while encased in a cast.

U.S. Pat. No. 4,549,547 to Brighton et al., entitled "Implantable Bone Growth Stimulator," issued Oct. 29, 1985, disclose a completely implanted bone growth stimulator with an external constant current source, and the device can be implanted and externally powered. U.S. Pat. No. 4,026,304 to Levy, entitled "Bone Generating Method and Device," issued May 31, 1977, discloses a self-contained prosthetic which stimulates bone growth by a train of electrical pulses and a prosthetic system comprising a substrate material that can be electrically driven to induce tissue infiltration into the substrate pore structure. U.S. Pat. No. 6,937,905 to Carroll et al., entitled "Osteogenesis Stimulator with Digital Signal Processing," issued Aug. 30, 2005, disclose a stimulator and a method for electrical stimulation of bone in which surface electrodes transmit an interferential current stimulation and a method for electrical stimulation of bone in which surface electrodes are positioned around an incision. The device described employs two cutaneous-surface mounted circuits controlled by a digital signal processor to produce and direct an interferential current that is nominally capable of somewhat precisely targeting of bone (or tissue) where osteogenesis is desired.

U.S. Patent Application 2004/0054379 to Carroll et al. entitled "Surface Electrical Stimulation for Increasing the quality and Quantity of Synovial Fluid in Joints," discloses a device for improving synovial fluid by applying electrical stimulation in a sequencing pattern. U.S. Pat. No. 5,397,338 to Grey et al., entitled "Electrotherapy Device," issued Mar. 14, 1995, disclose a flexible elastic sleeve including electrodes sewn into the sleeve that deliver electrical energy to tissues in and around joints. U.S. Pat. No. 4,313,438 to Greatbatch, entitled "Tissue Growth Control Apparatus and Method," issued Feb. 2, 1982, discloses an electrode that is implanted and provides germicidal and healing treatment, with first a direct voltage applied of one polarity and thereafter of the opposite polarity. U.S. Pat. No. 4,846,181 to Miller, entitled "Soft Tissue Wound Healing Therapy Utilizing Pulsed Electrical Stimulation," issued Jul. 11, 1989, discloses an active electrode positioned at a wound that provides pulsed electrical stimulation.

Those references disclose devices that employ some form of electrical stimulation to accelerate healing of both soft tissue and bone related trauma, and related infections. Most of these disclosures claims efficacious, cutaneous application of such electrical stimulation. Others disclose subcutaneous or implanted manifestations.

Cranio-facial bone repair and regeneration presents special challenges that relate to a variety of factors. Cranio-facial bone repair in the case of severe trauma, even using autologous material, is routinely complicated by lack of viable bone, short and long term disease process-related complications evident in existing tissue and bone, such as the degenerative condition of bone from long-term infection in sinus cavities, and post-operatively by factors such as the compromised vascular condition of the surgical site.

Low or largely non-existent levels of microcurrent at the site and in the immediate proximity of the wound affect the post-operative prognosis for cranio-facial bone repair and regeneration. In contrast to repairs to broken limbs where movement and stressing of the musculature and the limb itself routinely begin soon after the repair is affected, cranio-facial repairs exist in a state of relative stasis. In those cases where tissue has been compromised or replaced with other materials, such as frontal sinus obliteration where the sinus is filled with a compound such as hydoxyapatite, the prognosis for tissue and bone regeneration is problematic.

There is thus a present need for an apparatus that delivers pulsed or continuous micro-current stimulation to a site where tissue repair is desired, and which is implantable close to or at the wound. In particular, there is a need for an apparatus comprised of a harness of micro-scale electrodes attached to a power source and controller, and stabilized for placement on a substrate or patch made of a hypoallergenic, biodegradable material that is placed under the skin and absorbed by the patient as part of the treatment or healing process. There is particularly a present need for such a device with a primary application to cranial-facial conditions.

BRIEF SUMMARY OF THE INVENTION

The present invention comprises an apparatus for healing tissue comprising a substrate patch, a controller device, a plurality of micro-scale electrodes, and a power supply that is technologically flexible and can be upgraded to employ the latest in controller technology, power supplies, nanotechnology, and scientific findings in bone and soft tissue morphogenics. A preferred embodiment of the present invention provides a method to heal, repair, and remediate cranial (cathedral) bone trauma and repair.

The present invention comprises an apparatus and method for treating tissue of a patient. The apparatus preferably comprises a substrate implantable into a patient in proximity to a selected tissue of the patient; a plurality of electrodes disposed on or connected to the substrate for delivering microcurrent to the selected tissue; a controller for providing the microcurrent; and a port disposed at a skin surface or outside of the patient and connected to the plurality of electrodes and the controller.

The substrate may be a patch, may be non-woven, and may be biodegradable and absorbable into the patient's tissue. The substrate may be cuttable to fit an intended size. The substrate may comprise animal tissue or tissue cultured from the cells of the patient, or may any other biodegradable material. The substrate material is preferably hypoallergenic.

The electrodes are preferably disposed in a harness and/or network configuration. The electrodes preferably comprise silver or other conductive material, or carbon nanotubes. The electrodes may plug into the port. The apparatus or harness preferably comprises between approximately 25 and 75 electrodes; more preferably between approximately 30 and 60 electrodes; and most preferably between approximately 35 and 55 electrodes.

The controller is preferably a microcontroller. The microcurrent may pulse or reverse polarity. In one embodiment, the controller electrifies the electrodes in a plurality of patterns and thus provides stimulation in a plurality of patterns. The number of patterns provided can comprise any number and preferably comprise one hundred or more patterns and more preferably one thousand or more.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. As shown therein.

DETAILED DESCRIPTION OF THE INVENTION

Figure 1:
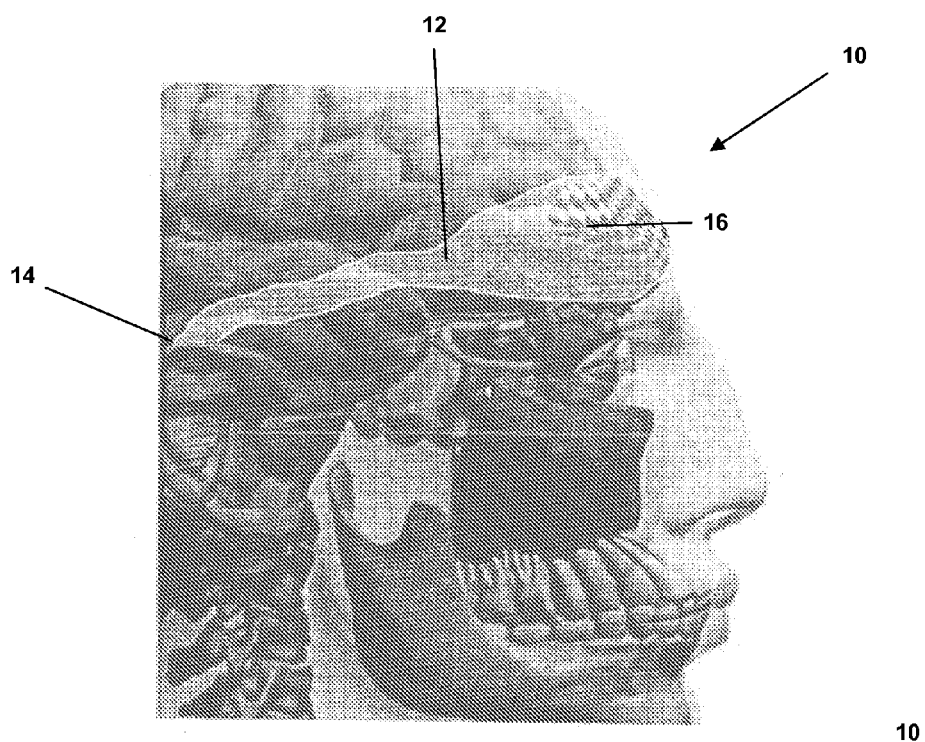
FIG. 1 is a side view illustrating a patient with the tissue treatment apparatus of the present invention.

The present invention relates to an implantable, microprocessor-controlled apparatus that delivers pulsed or continuous microcurrent stimulation to the site and immediate proximity of wounds with particular and primary application to cranio-facial conditions. The present invention aids in blood supply regeneration, bone growth, fusion of fractures, suppression of infection, integration of non-autologous materials with existing bone, to generally accelerate healing, and other therapeutic purposes. The medical apparatus and method is preferably used for treatment, repair and integration when bone or tissue replacement materials are used.

The present invention is an implantable, microprocessor-controlled apparatus that preferably delivers pulsed or continuous microcurrent stimulation, including direct, alternating, and interlerential current, preferably to the immediate proximity of wounds, injuries, or tissue in need of treatment or regeneration. The implantable, microprocessor-controlled apparatus comprises at least one harness of electrodes attached to a patch removably attached to a microcurrent-controlling device. The patch shape and size is preferably a function of the configuration of the wound and alternately shaped and sized in a generic configuration. The patch comprises a scalable technology, and can be cut to fit and flexibly provides practical applications in addition to cathedral bone injuries. The present invention preferably comprises a biodegradable, implantable, microprocessor-controlled, microcurrent-assisted, electro-stimulation apparatus attached to a stabilizing substrate for treatment or regeneration of tissue. The stabilizing substrate is preferably variously positionable and disposed in proximity to tissue to be treated, repaired or regenerated.

The patch is preferably attached to a plurality of electrodes which are preferably disposed in a harness configuration, comprising a network configuration on the patch. The electrodes preferably connect to a plug-in port preferably located behind a patient's ear or alternately located elsewhere as medically appropriate to the site of the wound. The electrodes are preferably configured in a plurality of networks to provide a broad array of patterns of stimulation.

Although embodiments of the present invention can comprise any number of electrodes greater than one, a preferred embodiment of the present invention comprises between 70 and 25 electrodes in a harness configuration, more preferably between approximately 60 and 30 electrodes and most preferably between approximately 55 and 35 electrodes. The electrodes are preferably disposed on a patch preferably implantably disposed on a wound that preferably provides one or more patterns of stimulation and more preferably more than 1,000 patterns of stimulation. An alternate embodiment of the present invention comprises reversing polarity of the electrodes, which preferably doubles the number of patterns of stimulation. The preferred embodiment of configurations of electrodes comprise a system that creates redundancy that improves the performance of the apparatus where recovery time is drawn out or the integrity of the apparatus, by design, deteriorates over time.

The electrodes disposed in the harness preferably comprise a conductive material, and more preferably one or more wires. The wires preferably comprise a strong material, such as a metal, including but not limited to silver, copper and gold, or other materials, including but not limited to insulated carbon nanotubes. The wire electrodes preferably comprise nano-wire or micro-wire, and alternately ultra-fine wire or another thickness of wire, and are alternately comprised of insulated carbon nanotubes with the exposed tip of each electrode preferably coated with silver or other conductive material. The electrodes are preferably disposed on a substrate, preferably a patch and alternately any covering. The electrodes are connected to a controller, preferably a micro controller or a microprocessor. The controller is preferably a small size between 1.0-2.0 millimeters in diameter and 0.1-0.2 millimeters in thickness and alternately any size. The controller preferably requires low current between 1.0-18 volts DC and preferably 1.0-9.0 volts DC. The present invention preferably employs state-of-the-art technology and is simple to use.

The electrodes are of an extremely small size and delicacy and the electrode configuration is preferably provided by a harness configured to position electrodes in a predetermined pattern. The electrodes are preferably pre-mounted on a suitable hypoallergenic and bio-degradable substrate or patch.

The substrate preferably comprises a non-woven biodegradable and bio-active material, including but not limited to similar tissue regeneration enhancing substances and including but not limited to a spun phosphorelated chitin impregnated with bone morphogenic proteins. The substrate is preferably disposed on or near a wound and alternately disposed on an alternate location.

The substrate preferably comprises a platform for initial placement of the harness and subsequently as it bio-degrades, the substrate preferably provides bioactive enhancements to the treatment or healing process for bone and surrounding tissue. The patch preferably bio-degrades with an efficacious effect on the wound. The substrate is preferably stabilizing and is trimmable or cut to any size or shape (e.g. with surgical scissors or other tool) prior to application to adjust to various wound sizes and configurations. This permits a surgeon to stock only a few sizes of substrates and to customize a substrate for any patient.

The substrate preferably comprises a durable material, on which the electrodes disposed in a harness are durably disposed. The substrate is alternately comprised of tissue, preferably tissue cultured from the patient's own cells and alternately comprises any biodegradable material. The substrate is preferably connected to electrodes disposed in a harness, or disposed near the electrodes disposed in a harness but optionally at any point.

The substrate is preferably implantable, attached to electrodes disposed in the harness that connect to a microcontroller. Thus the substrate may be implanted at any site on a patient, making installation easy. The substrate may be implanted at any site near or on a wound of a patient.

FIG. 1 shows the preferred embodiment of apparatus of the present invention 10 for treating or healing tissue. Apparatus 10 is disposed on the frontal sinus area of a patient after the surgeon makes an incision from ear to ear over the top of the cranium. The skin covering the forehead is then folded forward to the point where the area immediately above the eyebrows is accessible. The bone covering the sinus is resected leaving a flap-like piece to eventually close the wound, or alternately is removed completely. The sinus is cleaned, the drainage canal plugged, the sinus packed with the patient's fat harvested from the waist or other fatty area, and the sinus flap is replaced and anchored in place.

Alternatively, the sinus is packed with bone substitute such as one of the commercial formulations based on hydroxyapatite.

Prior to setting, the bone substitute material is sculpted to a contour consistent with the patient's existing bone. Upon completion of the repair, but before repositioning the forehead skin flap, the surgeon positions custom-configured patch 12 over the wound and positions electrodes 16 disposed in harness 14 on patch 12 in a pre-designated location immediately behind the patient's ear. Once patch 12 is fixed in place, the surgeon returns to the normal protocols for the procedure. The patch, being hypoallergenic and biodegradable, is rapidly absorbed by the patient as part of the treatment or healing process.

Figure 2:
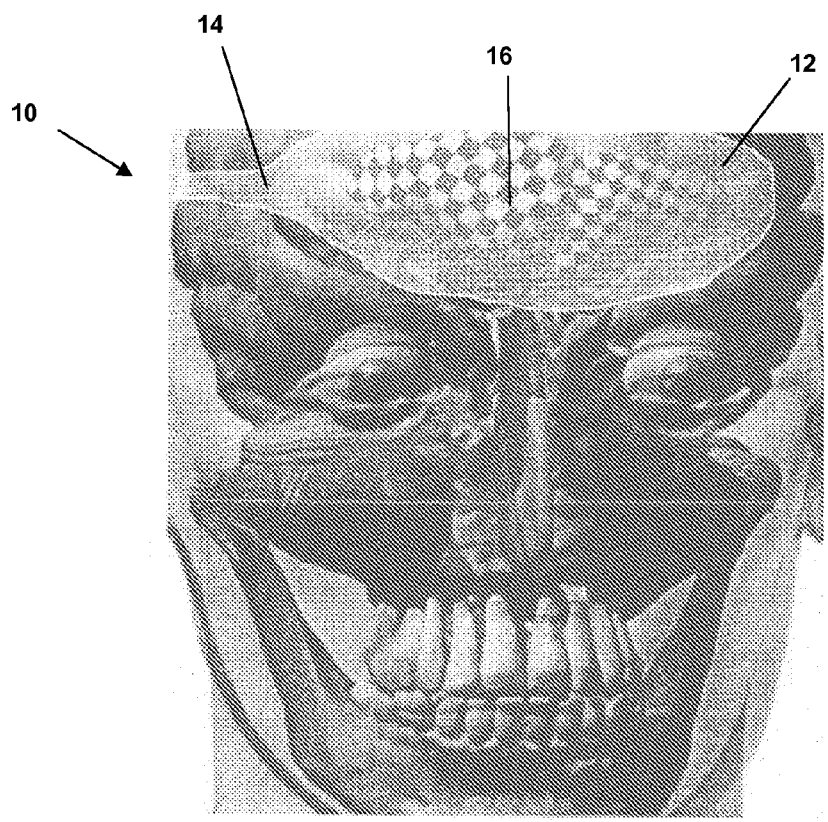
FIG. 2 is a front view illustrating a patient with the tissue treatment apparatus of the present invention.

FIG. 2 shows a front view of a preferred embodiment of apparatus 10 disposed on the frontal sinus area with electrodes 16 disposed in harness 14 on patch 12.

Figure 3:
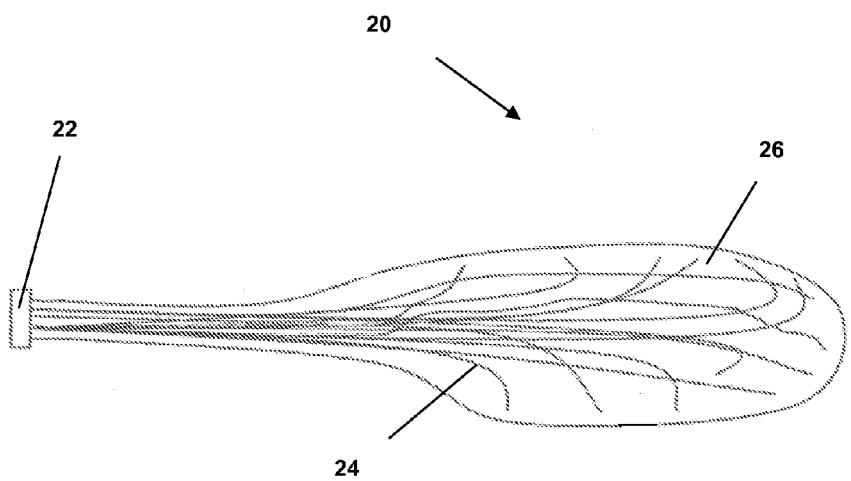
FIG. 3 is a side view drawing illustrating an implantable substrate patch with electrodes disposed in a harness according to an embodiment of the present invention.

FIG. 3 shows patch 20 with micro-current generation/controller device ports 22 attached to electrodes 24 in harness 26.

The patient may be a human or other animal. The substrate/patch may be used to treat wounds, fractures, diseases or even pain conditions.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed is:

1. An apparatus for treating tissue of a patient comprising:
an implantable substrate comprising an absorbable bioactive material providing bioactive enhancements to the treatment of bone and surrounding tissue from said substrate, said substrate implantable into a patient on the surface of bone and surrounding tissue of the patient;
a plurality of electrodes disposed on or connected to said substrate for delivering microcurrent from said plurality of electrodes to the bone and surrounding tissue;
a controller for providing said microcurrent; and
a port disposed at a skin surface or outside of the patient and connected to said plurality of electrodes.

2. The apparatus of claim 1 wherein said substrate is non-woven.

3. The apparatus of claim 1 wherein said substrate is biodegradable and absorbable into the patient's tissue.

4. The apparatus of claim 1 wherein said plurality of electrodes is disposed in a harness configuration.

5. The apparatus of claim 1 wherein at least one of said electrodes comprises a carbon nanotube.

6. The apparatus of claim 1 wherein at least one of said electrodes plugs into said port.

7. The apparatus of claim 1 wherein said controller provides said microcurrent in pulses.

8. The apparatus of claim 1 wherein said electrodes reverse polarity.

9. The apparatus of claim 1 wherein said substrate comprises animal tissue.

10. The apparatus of claim 1 wherein said substrate comprises tissue cultured from cells of the patient.

11. The apparatus of claim 1 wherein said controller provides a plurality of patterns of stimulation.

12. The apparatus of claim 11 wherein said plurality of patterns comprises more than 1000 patterns.

13. The apparatus of claim 11 wherein said plurality of patterns comprises more than 1000 patterns.

14. The apparatus of claim 1 wherein said substrate comprises a biodegradable material.

15. The apparatus of claim 1 wherein said substrate comprises chitin.

16. The apparatus of claim 1 wherein at least one of said electrodes comprises silver or other conductive material.

17. The apparatus of claim 1 wherein said controller is a microcontroller.

18. The apparatus of claim 1 wherein the plurality of electrodes comprises between approximately 25 and 75 electrodes.

19. The apparatus of claim 18 wherein the plurality of electrodes comprises between approximately 30 and 60 electrodes.

20. The apparatus of claim 19 wherein the plurality of electrodes comprises between approximately 35 and 55 electrodes.

21. The apparatus of claim 1 wherein said electrodes are in a network configuration.

22. The apparatus of claim 1 wherein said substrate is cuttable to fit an intended size.

23. The apparatus of claim 1 wherein said bone comprises a cranium bone.

24. The apparatus of claim 1 wherein said electrodes comprise micro-wire.

25. The apparatus of claim 1 wherein said electrodes comprise nano-wire.

26. The apparatus of claim 1 wherein said electrodes are implantable in a pre-designated location.

27. A method for treating tissue of a patient comprising:
implanting a substrate comprising an absorbable bioactive material into a patient on the surface of bone and surrounding tissue of the patient;
providing bioactive enhancements to the treatment of the bone and surrounding tissue from the substrate;
disposing a plurality of electrodes on or connected to the substrate;
providing a microcurrent via a controller;
delivering the microcurrent from the plurality of electrodes to the bone and surrounding tissue; and
connecting the electrodes to a port disposed at a skin surface or outside of the patient.

28. The method of claim 27 wherein the substrate is a patch.

29. The method of claim 27 comprising biodegrading and absorbing the substrate into the patient's tissue as part of the healing process.

30. The method of claim 27 further comprising disposing the plurality of electrodes in a harness configuration.

31. The method of claim 27 wherein at least one of said electrodes comprises a carbon nanotube.

32. The method of claim 27 further comprising plugging at least one of said electrodes plugs into the port.

33. The method of claim 27 wherein the plurality of electrodes comprises between approximately 25 and 75 electrodes.

34. The method of claim 33 wherein the plurality of electrodes comprises between approximately 30 and 60 electrodes.

35. The method of claim 23 wherein the plurality of electrodes comprises between approximately 35 and 55 electrodes.

36. The method of claim 27 comprising pulsing the microcurrent.

37. The method of claim 27 comprising reversing polarity of the electrodes.

38. The method of claim 27 comprising culturing cells from tissue of the patient and the substrate comprises the tissue cells.

39. The method of claim 27 comprising the controller causing the plurality of electrodes to electrify in a plurality of patterns.

40. The method of claim 39 wherein the plurality of patterns comprises more than 1,000 patterns.

41. The method of claim 27 wherein at least one of said electrodes comprises silver or other conductive material.

42. The method of claim 27 wherein said controller is a microcontroller.

43. The method of claim 27 further comprising networking the electrodes.

44. The method of claim 27 further comprising cutting the substrate to fit an intended size.

45. The method of claim 27 wherein the substrate comprises chitin.

46. The method of claim 27 wherein the bone comprises a cranium bone.

47. The method of claim 27 wherein the electrodes comprise nano-wire.

48. The method of claim 27 wherein the electrodes comprise micro-wire.

49. The method of claim 27 wherein the electrodes comprise ultra-fine-wire.

* * * * *